United States Patent
Kowaleski et al.

(10) Patent No.: US 7,282,619 B2
(45) Date of Patent: Oct. 16, 2007

(54) METHOD OF OPERATING A DEHYDROGENATION REACTOR SYSTEM

(75) Inventors: Ruth Mary Kowaleski, Cypress, TX (US); Robert Dielman Culp, Katy, TX (US)

(73) Assignee: Shell Oil Company, Houston, TX (US)

( * ) Notice: Subject to any disclaimer, the term of this patent is extended or adjusted under 35 U.S.C. 154(b) by 692 days.

(21) Appl. No.: 10/897,248

(22) Filed: Jul. 22, 2004

(65) Prior Publication Data

US 2005/0080306 A1    Apr. 14, 2005

Related U.S. Application Data

(60) Provisional application No. 60/510,909, filed on Oct. 14, 2003.

(51) Int. Cl.
*C07C 5/333* (2006.01)

(52) U.S. Cl. ................ 585/952; 585/440; 585/444; 585/445

(58) Field of Classification Search ........... 585/952, 585/440, 444, 445
See application file for complete search history.

(56) References Cited

U.S. PATENT DOCUMENTS

| | | |
|---|---|---|
| 4,758,543 A | 7/1988 | Sherrod et al. |
| 4,804,799 A | 2/1989 | Lewis et al. |
| 5,376,613 A | 12/1994 | Dellinger |
| 5,689,023 A | 11/1997 | Hamilton, Jr. |
| 5,824,619 A | 10/1998 | Sechrist et al. ............ 502/34 |
| 6,037,511 A | 3/2000 | Park et al. ............ 585/440 |
| 6,551,958 B1 | 4/2003 | Baier et al. |
| 2003/0144566 A1 | 7/2003 | Culp |

FOREIGN PATENT DOCUMENTS

EP    794004    6/2003

OTHER PUBLICATIONS

International Search Report for PCT/US2004/033614 of Apr. 11, 2005.
Written Opinion of PCT/US2004/033614 of Apr. 11, 2005.

*Primary Examiner*—Thuan Dinh Dang

(57) ABSTRACT

Described is a method for operating and shutting down a dehydrogenation reactor that contains a volume of dehydrogenation catalyst. After termination of the introduction of a dehydrogenation feed into the dehydrogenation reactor that is operated under dehydrogenation reaction conditions, a first cooling fluid comprising steam is introduced into the reactor for a first time period sufficient to cool the dehydrogenation catalyst contained in the dehydrogenation reactor to a second temperature. The introduction of the first cooling fluid is terminated followed by the introduction of a second cooling fluid for a second time period sufficient to cool the dehydrogenation catalyst contained in the dehydrogenation reactor to a third temperature that allows for the handling and removal of the dehydrogenation catalyst from the dehydrogenation reactor.

35 Claims, No Drawings

METHOD OF OPERATING A
DEHYDROGENATION REACTOR SYSTEM

This application claims the benefit of U.S. Provisional Application Ser. No. 60/510,909, filed Oct. 14, 2003.

The invention relates to a method of operating a dehydrogenation reactor system. The invention also relates to a method of shutting down an operating dehydrogenation reactor system used for the manufacture of styrene.

In the operation of hydrocarbon dehydrogenation reactor systems there is often a need to shut down an operating dehydrogenation process unit for a variety of reasons such as, for example, for the maintenance of the process unit or to remove and replace the dehydrogenation catalyst of the reactor system thereof. In styrene process units that use iron oxide based catalysts in the dehydrogenation of ethylbenzene to styrene, the shutdown of the reactor system typically requires a procedure for cooling down the iron oxide based catalyst contained therein prior to its removal.

One common method for cooling down the reactor catalyst is to pass steam over the bed of hot catalyst for a sufficient period of time to suitably reduce its temperature. This use of steam for catalyst cooldown, however, has been found to cause undesirable agglomeration of the catalyst particles of the catalyst bed. To solve the catalyst agglomeration problem, some have proposed the use of a modified cooldown procedure in which steam is first used to cool the temperature of the catalyst bed to a certain temperature that is above the temperature at which a significant amount of catalyst particle agglomeration occurs followed by the replacement of the use of the steam with that of nitrogen. The nitrogen is used to complete the cooling of the catalyst bed to a temperature level that permits removal of the catalyst from the reactor system.

While the modified cooldown procedure provides real advantages over the cooldown procedure that uses only a steam-containing fluid stream for the cooldown of a dehydrogenation reactor catalyst bed, it still does not resolve all the problems associated with the cooldown procedure. For instance, since nitrogen has a significantly lower heat capacity than does steam, the use of nitrogen as a catalyst cooldown fluid necessarily requires more time than does steam to cooldown a reactor catalyst bed. Also, the modified cooldown procedure does not completely solve the problem of catalyst agglomeration.

It is, thus, an object of this invention to provide a new method for shutting down an operating dehydrogenation reactor system where such method reduces some of the problems of catalyst agglomeration associated with other prior art dehydrogenation reactor shutdown procedures.

Accordingly, one invention is a single step cooldown procedure that includes contacting a dehydrogenation feed with a dehydrogenation catalyst under dehydrogenation reaction conditions to provide the dehydrogenation catalyst that is at a first temperature. The contacting of the dehydrogenation feed with the dehydrogenation catalyst is terminated followed by the contacting of the dehydrogenation catalyst with a carbon dioxide-containing cooling gas, comprising carbon dioxide. The contacting is conducted for a time period sufficient to reduce the temperature of the dehydrogenation catalyst to provide a cooled dehydrogenation catalyst having a temperature that is lower than the first temperature. The contacting of the dehydrogenation catalyst with the carbon dioxide-containing cooling gas is then terminated.

In an embodiment of the invention, a dehydrogenation reactor system is provided which comprises a dehydrogenation reactor defining a reaction zone and containing therein a dehydrogenation catalyst. A dehydrogenation feed is introduced into the dehydrogenation reactor that is operated under dehydrogenation reaction conditions such that the dehydrogenation catalyst is at a first temperature. The introduction of the dehydrogenation feed into said dehydrogenation reactor is then terminated followed by the introduction of a carbon dioxide-containing cooling gas, comprising carbon dioxide, into the dehydrogenation reactor for a time period sufficient to provide a cooled dehydrogenation catalyst having a temperature that is below the first temperature. The introduction of the carbon dioxide-containing cooling gas into the dehydrogenation reactor is thereafter terminated.

Another invention includes a method that comprises contacting a dehydrogenation feed with a dehydrogenation catalyst under dehydrogenation reaction conditions to thereby provide the dehydrogenation catalyst that is at a first temperature. Thereafter, the contacting of the dehydrogenation feed with the dehydrogenation catalyst is terminated. The dehydrogenation catalyst is then contacted with a first cooling gas, comprising steam, for a first time period sufficient to reduce the temperature of the dehydrogenation catalyst to a second temperature that is lower than the first temperature but greater than the condensation temperature of the first cooling gas. Thereafter, the contacting of the dehydrogenation catalyst with the first cooling gas is terminated. The dehydrogenation catalyst is then contacted with a second cooling gas, comprising a major portion carbon dioxide, for a second time period sufficient to reduce the temperature of the dehydrogenation catalyst to a third temperature that is lower than the second temperature.

Another embodiment of the invention includes a method of operating a dehydrogenation reactor system. In this method, a dehydrogenation reactor system is provided which comprises a dehydrogenation reactor defining a reaction zone and containing therein a dehydrogenation catalyst. A dehydrogenation feed is introduced into the dehydrogenation reactor operated under dehydrogenation reaction conditions such that the dehydrogenation catalyst is at a first temperature. Thereafter, the introduction of the dehydrogenation feed into the dehydrogenation reactor is terminated. A first cooling gas, comprising steam, is then introduced into the dehydrogenation reactor for a first time period sufficient to reduce the temperature of the dehydrogenation catalyst to a second temperature below the first temperature but greater than the condensation temperature of the first cooling gas. Thereafter, the introduction of the first cooling gas into said dehydrogenation reactor is terminated. A second cooling gas, comprising a major portion carbon dioxide, is then introduced into the dehydrogenation reactor for a second time period sufficient to reduce the temperature of the dehydrogenation catalyst to a third temperature below the second temperature.

Other objects and advantages of the invention will become apparent from the following detailed description and appended claims.

The inventive method is a particularly advantageous procedure for the shutdown of an operating dehydrogenation reactor system for the purpose of allowing access to or removal therefrom of the dehydrogenation catalyst of the dehydrogenation system. A dehydrogenation reactor system generally includes a dehydrogenation reactor vessel, having a reactor inlet for receiving a feed and a reactor outlet for discharging a reactor effluent. The dehydrogenation reactor vessel defines a dehydrogenation reaction zone and can contain dehydrogenation catalyst particles that are usually packed together to form a dehydrogenation catalyst bed.

The dehydrogenation catalyst of the dehydrogenation reactor system can be any known iron or iron oxide based catalyst that can suitably be used in the dehydrogenation of hydrocarbons. Such dehydrogenation catalysts include those catalysts that comprise iron oxide. The iron oxide of the dehydrogenation catalyst may be in any form and obtained from any source or by any method that provides a suitable iron oxide material for use in the iron oxide based dehydrogenation catalyst. One particularly desirable iron oxide based dehydrogenation catalyst includes potassium oxide and iron oxide.

The iron oxide of the iron oxide based dehydrogenation catalyst may be in a variety of forms including any one or more of the iron oxides, such as, for example, yellow iron oxide (goethite, FeOOH), black iron oxide (magnetite, $Fe_3O_4$), and red iron oxide (hematite, $Fe_2O_3$), including synthetic hematite or regenerated iron oxide, or it may be combined with potassium oxide to form potassium ferrite ($K_2Fe_2O_4$), or it may be combined with potassium oxide to form one or more of the phases containing both iron and potassium as represented by the formula $(K_2O)_x.(Fe_2O_3)_y$.

Typical iron based dehydrogenation catalysts comprise from 10 to 100 weight percent iron, calculated as $Fe_2O_3$, and up to 40 weight percent potassium, calculated as $K_2O$. The iron based dehydrogenation catalyst may further comprise one or more promoter metals that are usually in the form of an oxide. These promoter metals may be selected from the group consisting of Sc, Y, La, Mo, W, Cs, Rb, Ca, Mg, V, Cr, Co, Ni, Mn, Cu, Zn, Cd, Al, Sn, Bi, rare earths and mixtures of any two or more thereof. Among the promoter metals, preferred are those selected from the group consisting of Ca, Mg, Mo, W, Ce, La, Cu, Cr, V and mixtures of two or more thereof. Most preferred are Ca, Mg, W, Mo, and Ce.

Descriptions of typical iron-based dehydrogenation catalysts that can suitably be used as the dehydrogenation catalysts of the inventive method or process can be found in patent publications that include U.S. Patent Publication No. 2003/0144566 A1; U.S. Pat. No. 5,689,023; U.S. Pat. No. 5,376,613; U.S. Pat. No. 4,804,799; U.S. Pat. No. 4,758,543; U.S. Pat. No. 6,551,958 B1; and EP 0,794,004 B1, all of such patent publications are incorporated herein by reference.

The iron oxide based catalyst is prepared by any method known to those skilled in the art. The iron oxide based dehydrogenation catalyst comprising potassium oxide and iron oxide can, in general, be prepared by combining the components of an iron-containing compound and a potassium-containing compound, shaping these components to form particles, and calcining the particles. The promoter metal-containing compounds may also be combined with the iron-containing and potassium-containing components.

The catalyst components can be formed into particles such as extrudates, pellets, tablets, spheres, pills, saddles, trilobes, tetralobes and the like. One preferred method of making the iron based dehydrogenation catalyst is to mix together the catalyst components with water or a plasticizer, or both, and forming an extrudable paste from which extrudates are formed. The extrudates are then dried and calcined. The calcination is preferably done in an oxidizing atmosphere, such as air, and at temperatures upwardly to 1200° C., but preferably from 500° C. to 1100° C., and, most preferably, from 700° C. to 1050° C.

In the inventive method, the dehydrogenation catalyst is contacted with a dehydrogenation feed under dehydrogenation reaction conditions to thereby raise the temperature of the dehydrogenation catalyst to a first temperature that is a dehydrogenation temperature. More specifically, the dehydrogenation feed is introduced into the dehydrogenation reactor wherein it is contacted with the dehydrogenation catalyst bed. The dehydrogenation reactor is operated under dehydrogenation reaction conditions during the feed introduction step so as to raise the temperature of the dehydrogenation catalyst bed to a dehydrogenation temperature, or the first temperature.

It is recognized that the dehydrogenation reactor or dehydrogenation reactor system can include more than one dehydrogenation reactor or reaction zone. If more than a single dehydrogenation reactor is used, they may be operated in series or in parallel, or they may be operated independently from each other or under the same or different process conditions.

The dehydrogenation feed can be any suitable feed and, more particularly, it can include any hydrocarbon that is dehydrogenatable. Examples of dehydrogenatable hydrocarbons include isoamylenes, which can be dehydrogenated to isoprenes, and butenes, which can be dehydrogenated to butadiene. The preferred dehydrogenation feed comprises ethylbenzene, which can be dehydrogenated to styrene. The dehydrogenation feed can also include other components including diluents. It is common to use steam as a feed diluent when ethylbenzene is a feed component to be dehydrogenated to form styrene.

The dehydrogenation conditions can include a dehydrogenation reactor inlet temperature in the range of from about 500° C. to about 1000° C., preferably, from 525° C. to 750° C., and, most preferably, from 550° C. to 700° C. Thus, the first temperature of the dehydrogenation catalyst bed can range from about 500° C. to about 1000° C., more specifically, from 525° C. to 750° C., and, most specifically, from 550° C. to 700° C.

It is recognized, however, that in the dehydrogenation of ethylbenzene to styrene, the reaction is endothermic. When such a dehydrogenation reaction is carried out, it can be done so either isothermally or adiabatically. In the case where the dehydrogenation reaction is carried out adiabatically, the temperature across the dehydrogenation catalyst bed, between the dehydrogenation reactor inlet and the dehydrogenation reactor outlet, can decrease by as much as 150° C., but, more typically, the temperature can decrease from 10° C. to 120° C.

The reaction pressure is relatively low and can range from vacuum pressure upwardly to about 25 psia. The liquid hourly space velocity (LHSV) can be in the range of from about 0.01 $hr^{-1}$ to about 10 $hr^{-1}$, and preferably, from 0.1 $hr^{-1}$ to 2 $hr^{-1}$. As used herein, the term "liquid hourly space velocity" is defined as the liquid volumetric flow rate of the dehydrogenation feed, for example, ethylbenzene, measured at normal conditions (i.e., 0° C. and 1 bar absolute), divided by the volume of the catalyst bed, or the total volume of catalyst beds if there are two or more catalyst beds. When styrene is being manufactured by the dehydrogenation of ethylbenzene, it generally desirable to use steam as a diluent usually in a molar ratio of steam to ethylbenzene in the range of 0.1 to 20. Steam may also be used as a diluent with other dehydrogenatable hydrocarbons.

To shut down the dehydrogenation reactor system, the contacting of the dehydrogenation feed with the dehydrogenation catalyst is terminated. Upon this termination, the dehydrogenation catalyst particles of the reactor catalyst bed are at a first temperature that approximates the reactor temperature conditions existing immediately prior to the termination of the dehydrogenation feed introduction.

In a typical dehydrogenation reactor system the volume of the dehydrogenation catalyst contained in the dehydrogenation reactor vessel is significant. For example, commercial size dehydrogenation reactors can contain upwardly to about 100 to 400, or more, tons of catalyst per reactor vessel, which for a typical bed of iron oxide based dehydrogenation catalyst is a catalyst bed volume in the range of from about 100 cubic meters upwardly to about 400 cubic meters per reactor vessel. This large mass of catalyst at a high temperature must be cooled down to a temperature that preferably approaches an ambient temperature in order to allow for its handling and removal from the dehydrogenation reactor. Also, due to the large volume of catalyst, a cooling fluid is passed over the catalyst to accelerate the cooldown time to a time period that is commercially reasonable. In most commercial operations, it is desirable to minimize the down time of a process unit during maintenance and catalyst changeout in order to maximize product production.

Steam is a typical cooling fluid used to cooldown a dehydrogenation catalyst bed after its operation. But, it has been found that if steam is used to cool the temperature of the dehydrogenation catalyst bed below a certain level, various reactions can occur within the dehydrogenation catalyst bed that cause unwanted catalyst agglomeration. The presence of steam in a bed of dehydrogenation catalyst that comprises an iron based catalyst having a potassium ferrite phase can have a tendency to promote the decomposition of the potassium ferrite phase (e.g., $K_2Fe_2O_4$ and other potassium ferrites) to form potassium hydroxide (KOH) and iron oxide such as hematite ($Fe_2O_3$) and magnetite ($Fe_3O_4$). If the steam condenses in the cooler sections of the catalyst bed where iron oxide is present, the iron oxide tends to hydrate to form hydrated iron (FeOOH). The combination of potassium hydroxide (which is liquid above 360° C. up to its boiling point) and hydrated iron oxide tends to form a viscous, sticky mixture at the catalyst pellet surface and between catalyst pellets. Subsequent removal of steam or moisture from the dehydrogenation catalyst bed can result in converting the potassium hydroxide to potassium oxide, which serves to bind and cement the catalyst particles of the dehydrogenation catalyst bed into hard agglomerates thereby making the removal of the catalyst from the dehydrogenation reactor vessel and handling difficult and time consuming.

A modified shutdown procedure has been proposed which replaces the use of steam with nitrogen gas for cooldown at the lower temperatures in order to solve some of the problems associated with steam condensation and formation of hydrated iron. The use of nitrogen, however, has its own set of problems. Nitrogen gas has a significantly lower heat capacity than does steam; and, therefore, its use requires more volume of gas and a greater amount of time for cooldown procedure than when steam is used. Furthermore, the nitrogen atmosphere in the catalyst bed that has potassium hydroxide interspersed within it tends to promote, it is believed, the dehydration of the potassium hydroxide to potassium oxide ($K_2O$) and water. The presence of potassium oxide in the catalyst bed acts as a cement to agglomerate the catalyst particles.

The inventive method is a procedure for shutting down an operating dehydrogenation reactor system containing a bed of dehydrogenation catalyst that solves some of the aforementioned problems associated with the use of steam for the cooldown of the catalyst bed or with the use of steam in combination with nitrogen for the cooldown of the catalyst bed. The first step after the termination of the introduction of a dehydrogenation feed into a dehydrogenation reactor that has been operated under dehydrogenation conditions includes the introduction of steam as a first cooling fluid, or gas, into the dehydrogenation reactor to thereby contact the dehydrogenation catalyst with the first cooling fluid. The first cooling fluid, which comprises steam, is contacted with the dehydrogenation catalyst bed for a first time period that is sufficient to reduce the temperature of the dehydrogenation catalyst of the dehydrogenation catalyst bed to a second temperature that is below the first temperature.

Due to the availability and relatively low cost of steam, as well as its favorable properties as a heat transfer medium, it is desirable to achieve with the first cooling fluid the largest temperature differential between the second temperature and the first temperature as is permissible without incurring some of the problems noted hereinabove with the use of steam as a cooling fluid. It is therefore important for the temperature within the dehydrogenation reactor and catalyst bed to not be reduced during the first time period of cooling below the condensation temperature of the first cooling fluid. Thus, generally, the first cooling fluid comprises steam that is preferably slightly superheated and as it passes through the hot dehydrogenation catalyst bed it gains additional superheating. The first cooling fluid will, generally, comprise a predominant amount of steam, usually comprising more than 90 weight percent steam and, preferably, greater than 95 weight percent steam and, most preferably, greater than 99 weight percent steam.

Typically, steam is available as the first cooling fluid at a variety of pressures ranging from around 10 pounds per square inch absolute pressure (psia) upwardly to 500 psia or more. Generally, the steam that is available for use as a cooling fluid will be saturated steam or superheated steam; but, initially, as it passes through the hot dehydrogenation catalyst bed, which when the first cooling time period begins such hot dehydrogenation catalyst bed will be at temperatures exceeding 500° C., the steam picks up heat and gains additional superheat. The cooldown pressure within the dehydrogenation reactor vessel is generally in the range from below atmospheric upwardly to 40 psia, or greater, and for these cooldown pressures, it is best for the dehydrogenation catalyst temperature to be reduced to a second temperature during the first time period of no less than about 350° C., preferably, no less than 380° C., and, most preferably, no less than 400° C. Thus, the second temperature is less than the first temperature of the dehydrogenation catalyst bed as described above and can be in the range of from just below the first temperature to about 350° C., preferably, from less than 500° C. to 380° C., and, most preferably, from less than 500° C. to 400° C. The temperature of the first cooling fluid at the reactor outlet reflects the second temperature of the dehydrogenation catalyst.

Once the temperature of the dehydrogenation catalyst bed is reduced to the desired second temperature, as reflected by the temperature of the first cooling fluid at the reactor outlet, the introduction of the first cooling fluid into the dehydrogenation reactor vessel and contacting with the dehydrogenation catalyst is terminated.

In the step after the termination of the introduction of the first cooling fluid into the dehydrogenation reactor, a second cooling fluid, or gas, is introduced into the dehydrogenation reactor to thereby contact the dehydrogenation catalyst with the second cooling fluid. The second cooling fluid comprises carbon dioxide. The use of carbon dioxide is found to reduce some of the aforementioned problems associated with the use of other cooling fluids such as steam and nitrogen. Also, carbon dioxide has a higher heat capacity than nitrogen, which makes carbon dioxide more desirable than nitrogen as a heat removal fluid.

Table 1 presents the heat capacities of various gases. It is noted from the values presented in Table 1 that carbon dioxide has a significantly higher heat capacity than does nitrogen and water.

TABLE 1

Heat Capacities of Various Gases

| Gas/Temp. | Heat Capacities* at Given Temperature | | | | | |
|---|---|---|---|---|---|---|
| | 200° C. | 300° C. | 400° C. | 500° C. | 600° C. | 700° C. |
| $CO_2$ | 43.8 | 46.6 | 49.0 | 51.0 | 52.6 | 54.0 |
| $N_2$ | 29.8 | 30.3 | 30.9 | 31.4 | 31.9 | 32.4 |
| $H_2O$ | 34.9 | 36.0 | 37.2 | 38.4 | 39.7 | 40.9 |

*joules/mole/kelvin

It is desirable for the second cooling fluid to contain little or only minor amounts of oxygen, carbon monoxide, water, either as steam or liquid, and other undesirable components. But, the second cooling fluid, in addition to containing carbon dioxide, can include up to a remaining portion thereof of nitrogen. Thus, the second cooling fluid can comprise a portion thereof carbon dioxide and a remaining portion thereof nitrogen.

To gain some of the benefits of a reduced formation of potassium oxide in the dehydrogenation catalyst bed from the use of the carbon dioxide-containing second cooling fluid, the minimum concentration of carbon dioxide in the second cooling fluid should exceed 20 volume percent or even 25 volume percent of the total volume of the second cooling fluid. The larger the concentration of carbon dioxide in the second cooling fluid the greater the benefit resulting from a reduced potassium oxide formation.

The amount of nitrogen in the second cooling fluid can range upwardly to the remaining volume that is not carbon dioxide. Thus, the nitrogen concentration of the second cooling fluid can be in the range upwardly to 70 or 80 volume percent.

In order to have a heat removal capability (i.e., heat capacity) that is equivalent to steam, the second cooling fluid should have a concentration of carbon dioxide exceeding about 30 volume percent. Preferred, however, is for the carbon dioxide concentration of the second cooling fluid to exceed 50 volume percent of the total volume of the second cooling fluid and, most preferred, the carbon dioxide concentration exceeds 75 volume percent. Up to the remaining portion of the second cooling fluid that is not carbon dioxide can include nitrogen. It is recognized that due to its high heat capacity, higher concentrations of carbon dioxide in the second cooling fluid provide for better heat removal from the dehydrogenation catalyst bed. Thus, the second cooling fluid can also comprise more than 90 or even 95 volume percent carbon dioxide. Undesirable components of the second cooling fluid can be present in amounts less than 0.5 volume percent, preferably, less than 0.2 volume percent, and, most preferably, less than 0.1 volume percent.

The second cooling fluid is contacted with the dehydrogenation catalyst bed for a second time period that is sufficient to reduce the temperature of the dehydrogenation catalyst of the dehydrogenation catalyst bed to a third temperature that is below the second temperature. The third temperature should be low enough to allow for the handling of the cooled down dehydrogenation catalyst and will generally approach ambient temperature conditions. Thus, the third temperature of the dehydrogenation catalyst generally should be less than 50° C. to allow for its handling and removal from the dehydrogenation reactor. It is better, however, for the third temperature of the dehydrogenation catalyst to be less than 40° C., and, preferably, less than 35 or 30° C. From a practical standpoint, the third temperature of the dehydrogenation catalyst is no lower than atmospheric temperature. The temperature of the second cooling fluid at the reactor outlet reflects the third temperature of the dehydrogenation catalyst.

Once the temperature of the dehydrogenation catalyst bed is reduced to the desired third temperature, as reflected by the temperature of the second cooling fluid at the reactor outlet, the introduction of the second cooling fluid into the dehydrogenation reactor vessel and contacting with the dehydrogenation catalyst is terminated. The reduced third temperature is low enough to permit handling and easy removal of the dehydrogenation catalyst from the dehydrogenation reactor. The use of a carbon dioxide-containing cooling fluid can also provide for a faster cooldown period, and its use can lead to the formation of potassium carbonate in the dehydrogenation catalyst bed instead of the formation of potassium hydroxide and potassium oxide that are associated with undesirable catalyst agglomeration.

Another inventive method for cooling down a dehydrogenation catalyst includes a single step cooldown procedure that uses a carbon dioxide-containing cooling gas but does not use steam as a cooling fluid. By eliminating the use of a steam as a cooling fluid the problems and risks associated with the use of steam as a cooling fluid are eliminated. Also, if the carbon dioxide-containing cooling gas has a sufficiently high concentration of carbon dioxide, the rate of catalyst cooldown can actually be increased over the rate of catalyst cooldown when steam is used for cooldown.

The inventive single step cooldown procedure includes contacting a dehydrogenation feed with a dehydrogenation catalyst under dehydrogenation reaction conditions to provide the dehydrogenation catalyst that is at a first temperature. The contacting of the dehydrogenation feed with the dehydrogenation catalyst is terminated followed by the contacting of the dehydrogenation catalyst with a carbon dioxide-containing cooling gas, comprising carbon dioxide. The contacting is conducted for a time period sufficient to reduce the temperature of the dehydrogenation catalyst to provide a cooled dehydrogenation catalyst having a temperature that is lower than the first temperature. The contacting of the dehydrogenation catalyst with the carbon dioxide-containing cooling gas is then therafter terminated.

In another embodiment of the catalyst cooldown procedure that does not use steam as a cooling fluid, a dehydrogenation reactor system is provided which comprises a dehydrogenation reactor defining a reaction zone and containing therein a dehydrogenation catalyst. A dehydrogenation feed is introduced into the dehydrogenation reactor that is operated under dehydrogenation reaction conditions such that the dehydrogenation catalyst is at a first temperature. The introduction of the dehydrogenation feed into said dehydrogenation reactor is then terminated followed by the introduction of a carbon dioxide-containing cooling gas, comprising carbon dioxide, into the dehydrogenation reactor for a time period sufficient to provide a cooled dehydrogenation catalyst having a temperature that is below the first temperature. The introduction of the carbon dioxide-containing cooling gas into the dehydrogenation reactor is thereafter terminated.

The carbon dioxide-containing cooling gas used in the single step cooldown procedure can have the same properties and compositions as described above for the second cooling fluid. As for the temperature of the cooled dehydrogenation catalyst, in order to allow for handling and removal from the dehydrogenation reactor it generally should be less than 50° C. It is better, however, for the temperature to be less than 40° C., and, preferably, less than 35 or 30° C. From a practical standpoint, the temperature is no lower than atmospheric temperature.

Reasonable variations, modifications and adaptations can be made within the scope of the described disclosure and the appended claims without departing from the scope of the invention.

That which is claimed is:

1. A method, comprising:
   contacting a dehydrogenation feed with a dehydrogenation catalyst under dehydrogenation reaction conditions thereby providing said dehydrogenation catalyst that is at a first temperature;
   terminating the contacting of said dehydrogenation feed with said dehydrogenation catalyst;
   contacting said dehydrogenation catalyst with a carbon dioxide-containing cooling gas, comprising carbon dioxide, for a time period sufficient to reduce the temperature of said dehydrogenation catalyst to provide a cooled dehydrogenation catalyst having a temperature that is lower than said first temperature; and
   terminating the contacting of said dehydrogenation catalyst with said carbon dioxide-containing cooling gas.

2. A method as recited in claim 1, wherein said first temperature in the range of from about 500° C. to about 1000° C.

3. A method as recited in claim 2, wherein said carbon dioxide-containing cooling gas comprises at least 25 volume percent carbon dioxide.

4. A method as recited in claim 3, wherein said temperature is low enough to allow for the handling of said cooled dehydrogenation catalyst.

5. A method as recited in claim 4, wherein said temperature of said cooled dehydrogenation catalyst is less than 50° C.

6. A method as recited in claim 5, wherein said carbon dioxide-containing cooling gas comprises at least 50 volume percent carbon dioxide.

7. A method as recited in claim 6, wherein said temperature of said cooled dehydrogenation catalyst is less than 40° C.

8. A method as recited in claim 7, wherein said carbon dioxide-containing cooling gas comprises more than 95 volume percent carbon dioxide.

9. A method of operating a dehydrogenation reactor system, said method comprises:
   providing said dehydrogenation reactor system, which comprises a dehydrogenation reactor defining a reaction zone and containing therein a dehydrogenation catalyst;
   introducing a dehydrogenation feed into said dehydrogenation reactor operated under dehydrogenation reaction conditions such that said dehydrogenation catalyst is at a first temperature;
   terminating the introduction of said dehydrogenation feed into said dehydrogenation reactor;
   introducing a carbon dioxide-containing cooling gas, comprising carbon dioxide, into said dehydrogenation reactor for a time period sufficient to provide a cooled dehydrogenation catalyst having a temperature that is below said first temperature; and
   terminating the introduction of said carbon dioxide-containing cooling gas into said dehydrogenation reactor.

10. A method as recited in claim 9, further comprising:
    removing said cooled dehydrogenation catalyst from said dehydrogenation reactor.

11. A method as recited in claim 10, wherein said first temperature in the range of from about 500° C. to about 1000° C.

12. A method as recited in claim 11, wherein said carbon dioxide-containing cooling gas comprises at least 25 volume percent carbon dioxide.

13. A method as recited in claim 12, wherein said temperature is low enough to allow for the handling of said cooled dehydrogenation catalyst.

14. A method as recited in claim 13, wherein said temperature of said cooled dehydrogenation catalyst is less than 50° C.

15. A method as recited in claim 14, wherein said carbon dioxide-containing cooling gas comprises at least 50 volume percent carbon dioxide.

16. A method as recited in claim 15, wherein said temperature of said cooled dehydrogenation catalyst is less than 40° C.

17. A method as recited in claim 16, wherein said carbon dioxide-containing cooling gas comprises more than 95 volume percent carbon dioxide.

18. A method, comprising:
    contacting a dehydrogenation feed with a dehydrogenation catalyst under dehydrogenation reaction conditions thereby providing said dehydrogenation catalyst that is at a first temperature;
    terminating the contacting of said dehydrogenation feed with said dehydrogenation catalyst;
    contacting said dehydrogenation catalyst with a first cooling gas, comprising steam, for a first time period sufficient to reduce the temperature of said dehydrogenation catalyst to a second temperature that is lower than said first temperature but greater than the condensation temperature of said first cooling gas;
    terminating the contacting of said dehydrogenation catalyst with said first cooling gas; and
    contacting said dehydrogenation catalyst with a second cooling gas, comprising carbon dioxide, for a second time period sufficient to reduce the temperature of said dehydrogenation catalyst to a third temperature that is lower than said second temperature.

19. A method as recited in claim 18, wherein said first temperature in the range of from about 500° C. to about 1000° C.

20. A method as recited in claim 19, wherein said first cooling gas comprises predominantly steam.

21. A method as recited in claim 20, wherein said second temperature is in the range of from less than the first temperature to 350° C.

22. A method as recited in claim 21, wherein said second cooling gas further comprises a major portion carbon dioxide.

23. A method as recited in claim 22, wherein said third temperature is less than said second temperature.

24. A method as recited in claim 23, wherein said third temperature is less than 50° C.

25. A method as recited in claim 24, wherein said major portion carbon dioxide of second cooling gas is more than 95 volume percent.

26. A method as recited in claim 25, further comprising: removing said dehydrogenation catalyst from said dehydrogenation reactor.

27. A method of operating a dehydrogenation reactor system, said method comprises:
providing said dehydrogenation reactor system, which comprises a dehydrogenation reactor defining a reaction zone and containing therein a dehydrogenation catalyst;
introducing a dehydrogenation feed into said dehydrogenation reactor operated under dehydrogenation reaction conditions such that said dehydrogenation catalyst is at a first temperature;
terminating the introduction of said dehydrogenation feed into said dehydrogenation reactor;
introducing a first cooling gas, comprising steam, into said dehydrogenation reactor for a first time period sufficient to reduce the temperature of said dehydrogenation catalyst to a second temperature below said first temperature but greater than the condensation temperature of the first cooling gas;
terminating the introduction of said first cooling gas into said dehydrogenation reactor; and
introducing a second cooling gas, comprising a major portion carbon dioxide, into said dehydrogenation reactor for a second time period sufficient to reduce the temperature of said dehydrogenation catalyst to a third temperature below said second temperature.

28. A method as recited in claim 27, further comprising: removing said dehydrogenation catalyst from said dehydrogenation reactor.

29. A method as recited in claim 28, wherein said first temperature in the range of from about 500° C. to about 1000° C.

30. A method as recited in claim 29, wherein said first cooling gas comprises predominantly steam.

31. A method as recited in claim 30, wherein said second temperature is in the range of from less than the first temperature to 350° C.

32. A method as recited in claim 31, wherein said second cooling gas comprises a major portion carbon dioxide.

33. A method as recited in claim 32, wherein said third temperature is less than said second temperature.

34. A method as recited in claim 33, wherein said third temperature is less than 50° C.

35. A method as recited in claim 34, wherein said major portion carbon dioxide of second cooling gas is more than 95 volume percent.

* * * * *